United States Patent
Winiski

(10) Patent No.: US 10,125,347 B2
(45) Date of Patent: Nov. 13, 2018

(54) METHOD FOR STIMULATING THE EXPRESSION OF SPECIFIC TISSUE MORPHOLOGIES IN FILAMENTOUS FUNGI

(71) Applicant: Jacob Winiski, Troy, NY (US)

(72) Inventor: Jacob Winiski, Troy, NY (US)

(73) Assignee: ECOVATIVE DESIGN, LLC, Green Island, NY (US)

(*) Notice: Subject to any disclaimer, the term of this patent is extended or adjusted under 35 U.S.C. 154(b) by 252 days.

(21) Appl. No.: 14/745,881

(22) Filed: Jun. 22, 2015

(65) Prior Publication Data

US 2016/0002589 A1    Jan. 7, 2016

Related U.S. Application Data

(60) Provisional application No. 62/021,240, filed on Jul. 7, 2014.

(51) Int. Cl.
| | |
|---|---|
| *C12N 1/14* | (2006.01) |
| *C12N 1/20* | (2006.01) |
| *C12N 1/18* | (2006.01) |

(52) U.S. Cl.
CPC ............ *C12N 1/14* (2013.01); *C12N 1/18* (2013.01); *C12N 1/20* (2013.01)

(58) Field of Classification Search
CPC ... C12N 1/14; C12N 1/22; C12N 1/18; C12N 1/20; C12N 3/00
See application file for complete search history.

(56) References Cited

U.S. PATENT DOCUMENTS

| | | | | |
|---|---|---|---|---|
| 2008/0046277 | A1* | 2/2008 | Stamets | A01N 63/04 705/308 |
| 2008/0295399 | A1* | 12/2008 | Kawai | A01G 1/04 47/1.1 |
| 2012/0315687 | A1* | 12/2012 | Bayer | C12N 1/14 435/254.1 |
| 2014/0038619 | A1* | 2/2014 | Moulsley | H04B 7/024 455/446 |

OTHER PUBLICATIONS

Sapak et al. (2008) Intl J Agric Biol 10(2): 127-132.*

* cited by examiner

*Primary Examiner* — Lisa J Hobbs
(74) *Attorney, Agent, or Firm* — Francis C. Hand; Carella, Byrne, et al.

(57) ABSTRACT

The method of making a composite biomaterial employs a binding organism (a filamentous fungi that produce mycelium) based on the material physical properties required for the composite biomaterial and a modulating organism (bacteria, fungus or yeast) based on a desired effect of the modulating organism on the binding organism. The modulating organism is selected based on the desired effect on the binding organism.

22 Claims, 5 Drawing Sheets

METHOD FOR STIMULATING THE EXPRESSION OF SPECIFIC TISSUE MORPHOLOGIES IN FILAMENTOUS FUNGI

This invention claims priority of Provisional Patent Application 62/021,240 filed Jul. 7, 2014.

This invention relates to a method for stimulating the expression of specific tissue morphologies in filamentous fungi.

BACKGROUND OF THE INVENTION

In nature, fungi produce a number of biochemical and morphological responses to other microorganisms as a means of competing for resources. These interactions typically fall into two categories: antagonism from a distance (in which antagonistic bioactive compounds are leached into the environment to inhibit the growth of surrounding organisms), and physical antagonism (in which the fungus comes into physical antagonistic contact with a competing microorganism).

Fungi also have a dynamic range of responses to the antagonism of competing microorganisms, including rapid recovery, fruiting and sporulation, and the creation of physical barriers between the mycelial mass and the competing organism (such as thickened zones of mycelium at the interface, extra-cellular pigmentation/melanin).

As is known, U.S. patent application Ser. No. 12/001,556, filed Dec. 12, 2007, now U.S. Pat. No. 9,485,917, issued Nov. 8, 2016, describes various techniques for making a biomaterial composed of a substrate of discrete particles and a network of interconnected mycelia cells extending through and around the discrete particles and bonding discrete particles together. This biomaterial leverages the tenacious strength of fungal vegetative mycelium.

It is an object of the invention to obtain specific tissue morphologies in the fungus used for making composite materials by placing the binding organism in competitive contact with a modulating organism.

It is another object of the invention to selectively inhibit the growth of a binding organism used in making a biomaterial via application of a modulating organism to the binding organism.

Briefly, the invention provides a method for stimulating the expression of specific tissue morphologies in filamentous fungi via interactions with competing microorganisms. These tissue morphologies are described within the context of biomaterial production utilizing the vegetative mycelium of filamentous fungi, and the morphologies produced via the described competitive interactions may provide unique material physical properties within the said context. Relationships and interactions are described between A) a binding organism (the filamentous fungus being cultivated as a biomaterial), and B) a modulating organism (a microorganism introduced to the binding organism in order to elicit the expression of tissue morphology specific to the competitive interaction of the binding organism with the modulating organism and/or to completely inhibit the growth of the binding organism as a means of selectively controlling the boundaries of growth of the binding organism.

The process stimulates multiple tissue morphologies, with each providing particular functionalities within a given mycelium-based biomaterial based on the organisms selected and the method of modulating organism dispersal in relation to the binding organism. The specific interactions, and the results of those specific interactions, are additionally controlled by the selection of organisms based on A) application, B) environmental context, C) nutritive context, and D) ecological context.

In particular, the invention provides a method of making a composite biomaterial comprising the steps of selecting a binding organism based on the material physical properties required for the composite biomaterial and selecting a modulating organism based on a desired effect of the modulating organism on the binding organism.

The method requires the steps of inoculating a mass of discrete substrate particles with the binding organism; applying the modulating organism to the combination of binding organism and discrete substrate particles; and incubating the combination of binding organism, discrete substrate particles and modulating organism in an environment that is conducive to the growth of both the binding organism and modulating organism to produce a composite biomaterial having the discrete substrate particles bound together by the binding organism and the modulating organism imparting said desired effect on the binding organism.

These and other objects of the invention will become more apparent from the following detailed description taken in conjunction with the accompanying drawings wherein.

Figure 1:
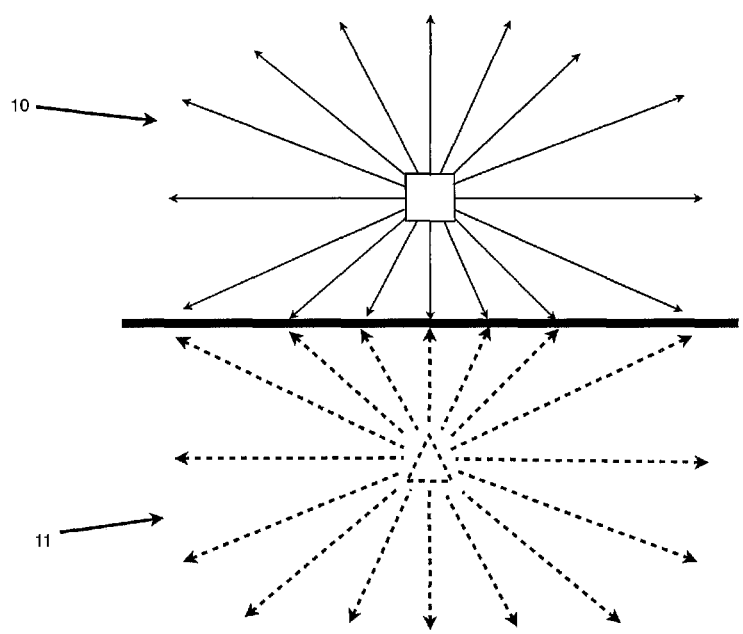
FIG. 1 illustrates a schematic representation of a cross-section of a binding organism on a modulating organism with a growth boundary therebetween.

Referring to FIG. 1, by placing a binding organism 10 on a modulating organism 11 in binary opposition to one another a clear boundary of interaction is created at the interface. This can function as a method of describing specific growth boundaries for the binding organism; the binding organism can be restricted to growing and expanding within defined parameters within a given volume or two-dimensional plane.

Figure 2:
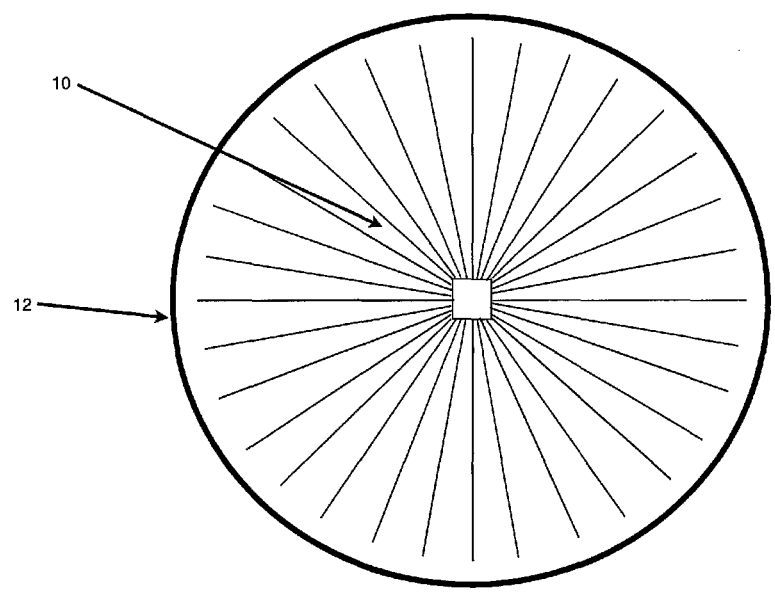
FIG. 2 illustrates a schematic representation of a binding organism growing without the presence of a modulating organism.

Referring to FIG. 2, wherein like reference characters indicate like parts as above, a binding organism 10 growing on a plate 12 without a modulating organism provides a smooth-looking appearance at a top surface.

Figure 3:
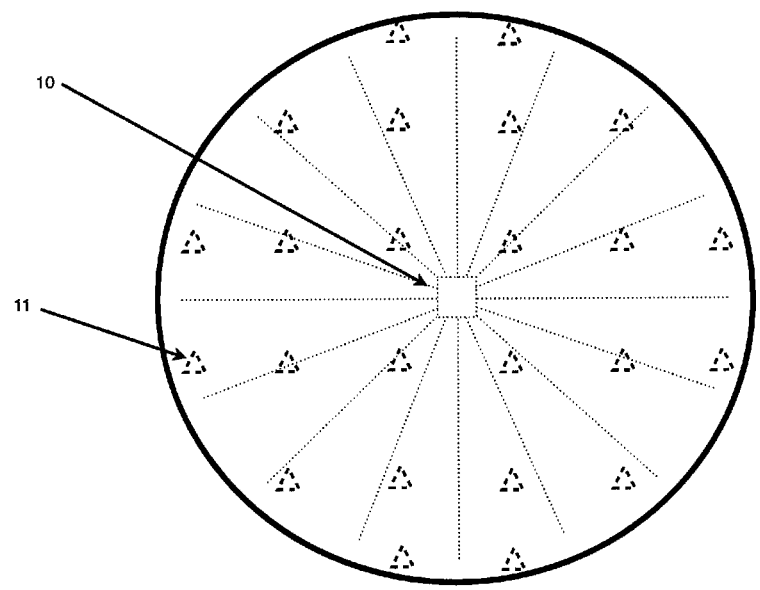
FIG. 3 illustrates a schematic representation of a binding organism growing with the presence of a modulating organism.

Referring to FIG. 3, wherein like reference characters indicate like parts as above, the binding organism 10 is grown with the modulating organism 11 homogeneously disbursed throughout the growth medium. In this case, the binding organism 10 is the only growth visually apparent, but the overall density of growth has been reduced due to the interaction of the modulating organism 11.

The "growth medium" is the nutrient substrate that the binding and modulating organisms are growing on. This is most often discrete lignocellulose particles.]

By homogeneously disbursing the modulating organism 11 throughout the volume of the growing binding organism 10, the overall density of the binding organism's mycelial colonization can be reduced via the competitive action of the modulating organism 11.

This method can be used for producing mycelium-based materials that require a reduced density of mycelial colonization without the need for chemical, nutritive, or environmental retardation of colonization.

Figure 4:
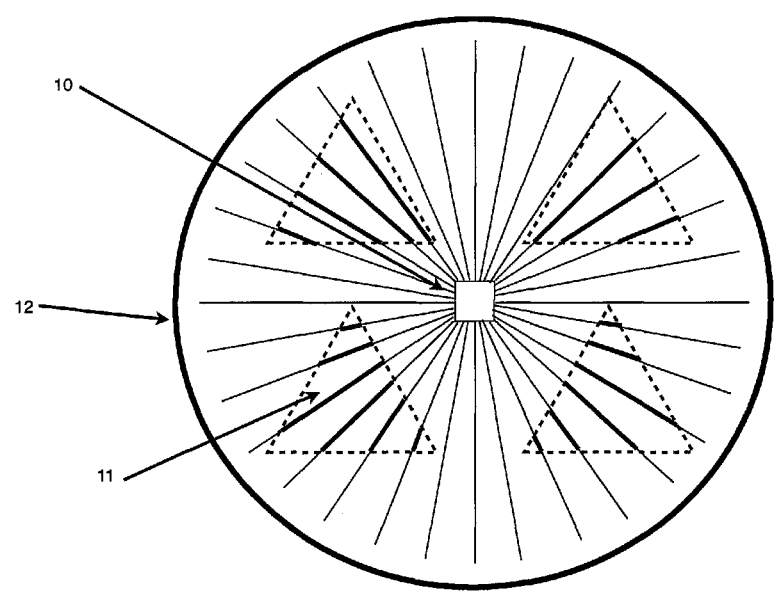
FIG. 4 illustrates a schematic representation of a binding organism expanding over a modulating organism on a plate.

Referring to FIG. 4, wherein like reference characters indicate like parts as above, by controlling the capacity of the modulating organism 11 to utilize the nutrition and environmental context, while also controlling the selection of binding organism 10 and modulating organism 11, a relationship can be developed that results in the binding organism 10 expressing a denser quality of mycelial colonization when in contact with the modulating organism 11 than would be typical. This can be utilized for increasing the density of growth for a given mycelium-based biomaterial, thereby modulating the material's flexural strength, compressive strength, thermal characteristics or stiffness.

As illustrated, the binding organism 10 has expanded over top of the modulating organism 11 (located at 4 points along the outside of the culture plate 12), leading to denser mycelial colonization of the binding organism 10 when coming into contact with the modulating organism 11.

When placed in binary opposition either the binding organism 10, the modulating organism 11, or both organisms can produce extra-cellular pigments 13 (such as melanin) at the interface between the two organisms. Based on species selection, this interaction can produce specific aesthetic results, which can be used to pigment the surface (or selected areas of the surface) of a given mycelium-based biomaterial.

A pigmentation response during binary interaction of a binding organism 10 with a modulating organism 11 resulted in a very dense production and depositing of melanin 13 at an interface between the two organisms.

Figure 5:
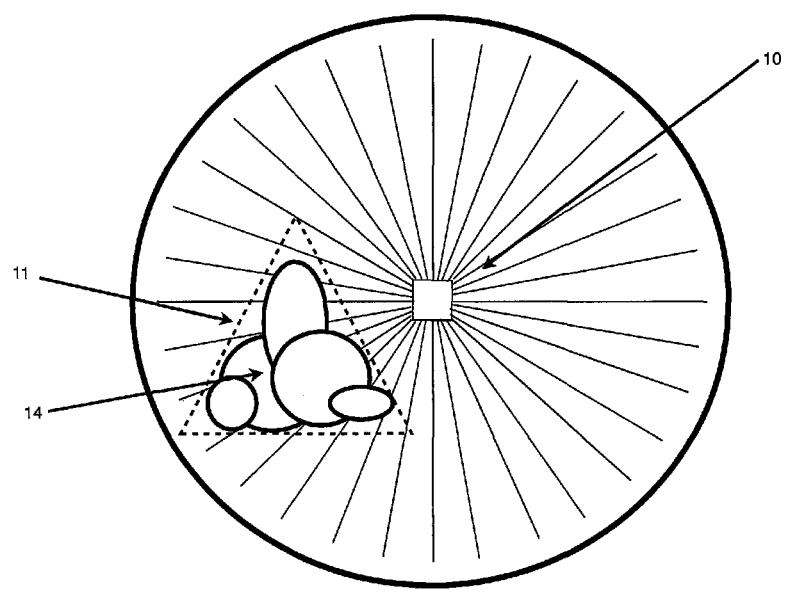
FIG. 5 illustrates a schematic representation of primordium development in response to a modulating organism.

Referring to FIG. 5, wherein like reference characters indicate like parts as above, by either placing the binding organism 10 and modulating organism 11 in a binary interaction, or by otherwise disbursing the modulating organism 11 throughout the mass of the binding organism 10, the induction of primordia/sporocarps can occur. Depending on the maturity and location of sporocarps on the given mycelium-based biomaterial, the strength and/or cushioning characteristics of the material can be increased.

As illustrated, in response to the modulating organism 11, the binding organism 10 (the only growth visually apparent) expanded and covered a selectively placed modulating organism 11, at which point, the binding organism 10 developed a large primordium 14 in the exact footprint of the modulating organism 12.

Based on organism selection, and placement of the binding organism 10 with the modulating organism 11, a thickened and/or aerial quality of vegetative growth can be induced at the interface between the binding organism 10 and the modulating organism 11. In this case, the thickened mycelium can impart additional cushioning or strength characteristics to the given mycelium-based biomaterial.

By homogeneously disbursing the modulating organism 11 throughout the binding organism 10, or selectively disbursing the modulating organism 11, and depending on organism selection, a generalized aerial quality of vegetative growth can be achieved. This aerial growth can provide additional cushioning and aesthetic characteristics to a given mycelium-based biomaterial.

A "fuzzy" aerial mycelium expressed across the surface of a mycelium-based biomaterial via the homogeneous disbursing of a modulating organism 11 throughout the volume of the binding organism 10.

The method for stimulating the expression of specific tissue morphologies in filamentous fungi comprises the following process steps:

1. Select a binding organism based on the desired material performance, as well as nutritive and environmental context for cultivation.

Examples of a binding organism would be filamentous fungi that produce mycelium that has attractive material physical properties based on the intended application (for example, high tensile strength for application as a low-density packaging material). Particularly, a filamentous fungi from the Basidiomycetes, such as *Ganoderma tsugae, Trametes hirsuta*, or *Ganoderma oregonense*.

2. Select a modulating organism based on the desired effect on the binding organism, desired method of disbursal, and nutritive and environmental context for cultivation. The modulating organisms ecological niche in relation to the binding organism's ecological niche should be considered, as well as the modulating organisms ability to utilize the nutritive and environmental context.

Examples of a modulating organism would be fungi or bacteria that specifically demonstrate a competitive/antagonistic dynamic with the binding organism. Examples include, but are not limited to:
   Bacteria: *Pseudomonas* sp., and *Bacillus* sp.
   Fungi: Zygomycetes, such as *Rhizopus* sp. and *Mucor* sp., Ascomycetes, such as *Aureobasidium* sp., *Trichoderma* sp., *Penecillium* sp., *Chrysonillla* sp., and *Aspergillus* sp. Basidiomycetes, such as *Phanerochaete* sp., *Trichaptum* sp., *Stereum* sp., *Phlebia* sp., *Laetiporus* sp., and *Peniophora* sp. Yeast, such as *Saccharomyces* sp.

3. Inoculate the target media for colonization/supporting mycelia colonization with the binding organism. This is the discrete particles to be bound together into a composite material by the mycelium of the binding organism, most often discrete lignocellulose particles (such as agricultural by-products or wood particles).

4. Disburse the modulating organism in relation to the binding organism by:
   a.) Placing the two organisms in a binary interaction, creating a single interface.
   b.) Homogeneously disbursing the modulating organism throughout the mass of the binding organism.
   c.) Selectively placing the modulating organism through, on, or in opposition to a portion of the overall mass of the binding organism via 4a or 4b.

5. Incubate the combination of binding and modulating organism within the desired environmental conditions until the desired quality of mycelial growth and tissue morphology has been achieved.

This step is highly specific to the intended application. For instance, if the intention is to induce primordia along the interface between the modulating and binding organism to provide a cushioning characteristic, and primordia 2 cm tall are required to achieve the desired cushioning characteristic, incubation would continue until the primordia reach a height of 2 cm.

6. Further process the biomaterial as necessary
   This is the composite material made up of the discrete lignocellulose particles bound together by the mycelium of the binding organism (which has had a particular expression induced by the modulating organism, and/or had its growth boundaries defined by inhibition of the modulating organism).

EXAMPLES

Example 1 Selection of Binding and Modulating Organism

1] Select nutrition for supporting the growth of the binding organism
2] Select a binding organism appropriate for the nutrition and environment for cultivation. For example, if using virgin lignocellulose a primary wood decomposing species should be selected.
3a] Select a modulating organism with an inferior ability to exploit the nutrition selected as compared to the binding organism. For example, if using pine substrate a species that cannot utilize pine, or utilize pine to the extent as the selected binding organism, should be selected.
3b] Select a modulating organism with an inferior growth rate than that of the selected binding organism. In this instance the binding organism out-paces the modulating organism, leading to domination of resources/nutrition.
3c] Select a modulating organism that is significantly effected by the competitive/antagonistic behavior of the binding organism. In this base the binding organism out-competes the modulating organism, leading to domination of resources/nutrition.
3d] Select a modulating organism that is inappropriate for the environmental conditions for colonization. For example, if the temperature for cultivation is 80 F, and the binding organism grows appropriately at 80 F, then a modulating organism that does not grow appropriately at 80 F should be selected.

Example 2 Disbursal of a Modulating Organism Through, or in Relation to, the Mass of the Binding Organism 1] Inoculate a given mass of lignocellulose substrate with a primary saprophyte binding organism.
2a] Homogeneously mix the modulating organism inoculum with the lignocellulose substrate.
2b] Homogeneously mix the modulating organism inoculum into a selected portion of the lignocellulose substrate.
2c] Apply the modulating organism inoculum to the entire surface, or a selected portion of the entire surface of the lignocellulose substrate mass.
3] Incubate the inoculated lignocellulose until the desired quality of colonization and tissue morphology has been achieved.
4] Further process the mycelium biomaterial as desired.

Example 3 Using Binary Stand-Off to Define Growth Boundaries for the Binding Organism within a Mass of Lignocellulose Substrate 1] In layers apply lignocellulose substrate to a bed.
2] Selectively disburse the binding organism inoculum into the positive space (area in 2-dimensions where the binding organism is desired to grow).
3] Selectively disburse the modulating organism inoculum into the negative space (area in 2-dimensions where the binding organism is not desired to grow). A modulating organism that cannot utilize the lignocellulose nutrition being utilized should be selected.
4] Repeat steps 1-3 until a volume of lignocellulose substrate has been built, with the volume of desired binding organism growth defined in three dimensions within the mass via the selective placement of binding and modulating organism inoculum.
5] Incubate the lignocellulose mass until the binding organism has reached the desired stage of colonization and expresses the desired tissue morphology.
6] Remove the colonized substrate from the non-colonized substrate.
7] Further process the colonized mass as desired.

Example 4 Decreasing or Increasing the Density of Mycelial Colonization within a Biomaterial Consisting of Mycelium Binding Together Discreet Particles of Lignocellulose 1] Select a binding organism appropriate for the target substrate for colonization.
2a] To increase density select a modulating organism previously determined to induce an increase in mycelial density in the binding organism.
2b] To decrease the density select a modulating organism previously determined to induce a decrease in mycelial density in the binding organism.
3] Incubate the inoculated substrate until the desired quality of colonization has been achieved.
4] Process the colonized substrate as desired.

Example 5 Inducing Pigmentation on the Surface of a Mycelium-Based Biomaterial 1] Select a binding organism that is both appropriate for the target substrate intended for colonization and has been previously identified as producing pigmentation in the vegetative mycelium.
2] Follow the steps of modulating organism distribution and incubation of any of examples 1-4.

Example 6 Inducing Sporocarp Development on the Surface of a Mycelium-Based Biomaterial 1] Select a binding organism that is both appropriate for the target substrate and has been shown to develop primordia in response to competition with a modulating organism.
2] Follow the steps of modulating organism distribution and incubation of any of examples 1-5.

Example 7 Inducing Thickened and/or Aerial Mycelium on the Surface/Through the Volume of a Biomaterial Consisting of Mycelium Binding Together Discreet Particles of Lignocellulose 1] Select a binding organism that is both appropriate for the target substrate and has been shown to develop aerial vegetative mycelium in response to competition with a modulating organism.
2] Follow the steps of example 2.

What is claimed is:
1. A method of making a composite biomaterial comprising the steps of
   selecting a binding organism based on the material physical properties required for the composite biomaterial;
   selecting a modulating organism based on a desired effect of the modulating organism on the binding organism;
   inoculating a mass of discrete substrate particles with the binding organism;
   applying the modulating organism to the combination of binding organism and discrete substrate particles; and incubating the combination of binding organism, discrete substrate particles and modulating organism in an environment that is conducive to the growth of both the binding organism and modulating organism to produce a composite biomaterial having the discrete substrate particles bound together by the binding organism and the modulating organism imparting said desired effect on the binding organism.

2. A method as set forth in claim 1 wherein said desired effect is one of cultivation of the binding organism, an antagonistic/inhibitory effect on the binding organism when placed in contact with the modulating organism, an inhibitory effect that induces an expression of specific morphology or inhibition of growth on the binding organism.

3. A method as set forth in claim 1 wherein the inoculated substrate particles are placed into a desired geometry for growth of both the binding organism and modulating organism.

4. A method as set forth in claim 1 wherein the inoculated substrate particles are placed into a desired geometry for growth of both the binding organism and modulating organism after said step of applying the modulating organism to the combination of binding organism and discrete substrate particles.

5. A method as set forth in claim 1 wherein said step of applying the modulating organism to the combination of binding organism and discrete substrate particles occurs before said step of incubating.

6. A method as set forth in claim 1 wherein said step of applying the modulating organism to the combination of binding organism and discrete substrate particles occurs during said step of incubating.

7. A method as set forth in claim 1 wherein the composite biomaterial is dried to less than 10% moisture for application as a low-density packaging product.

8. A method as set forth in claim 1 wherein the composite biomaterial is heat compressed for application in high-density engineered wood applications.

9. A method as set forth in claim 1 wherein the binding organism is a filamentous fungi that produce mycelium.

10. A method as set forth in claim 9 wherein said filamentous fungi is a Basidiomycete including one of *Ganoderma tsugae*, *Trametes hirsute*, and *Ganoderma oregonense*.

11. A method as set forth in claim 1 wherein the modulating organism is a bacteria.

12. A method as set forth in claim 11 wherein the bacteria is one of *Pseudomonas* sp. and *Bacillus* sp.

13. A method as set forth in claim 1 wherein the discrete substrate particles are lignocellulosic particles.

14. A method as set forth in claim 1 wherein the binding organism is a filamentous fungi that produce mycelium and the composite biomaterial has the discrete substrate particles thereof bound together by the mycelium produced by the binding organism.

15. A method of making a composite biomaterial comprising the steps of
selecting a binding organism of filamentous fungi for producing mycelium based on the material physical properties required for the composite biomaterial;
selecting a modulating organism from one of bacteria, fungus and yeast based on a desired effect of the modulating organism on the binding organism;
inoculating a mass of discrete lignocellulose substrate particles with the binding organism;
applying the modulating organism to the combination of binding organism and discrete substrate particles; and
incubating the combination of binding organism, discrete substrate particles and modulating organism in an environment that is conducive to the growth of both the binding organism and modulating organism to produce a composite biomaterial having the discrete substrate particles bound together by the binding organism and the modulating organism imparting said desired effect on the binding organism.

16. The method of claim 15 wherein the modulating organism is applied to the combination of binding organism and discrete substrate particles to induce growth of primordia/sporocarps on the produced composite biomaterial to provide a cushioning characteristic to the produced composite biomaterial.

17. The method of claim 15 further comprising the step of producing a pigmentation response at an interface between the modulating organism and the binding organism during a binary interaction of the modulating organism and the binding organism.

18. A method as set forth in claim 1 wherein the modulating organism is a fungus.

19. A method as set forth in claim 18 wherein the fungus is one of a Zygomycete, Ascomycetes and Basidiomycete.

20. A method as set forth in claim 18 wherein the fungus is one of *Rhizopus* sp. and *Mucor* sp.; *Aureobasidium* sp., *Trichoderma* sp., *Penecillium* sp., *Chrysonillia* sp., and *Aspergillus* sp.; and *Phanerochaete* sp., *Trichaptum* sp., *Stereum* sp., *Phlebia* sp., *Laetiporus* sp., and *Peniophora* sp.

21. A method as set forth in claim 1 wherein the modulating organism is a yeast.

22. A method as set forth in claim 21 wherein the yeast is *Saccharomyces* sp.

* * * * *